US010836791B2

(12) United States Patent
Heidl et al.

(10) Patent No.: US 10,836,791 B2
(45) Date of Patent: Nov. 17, 2020

(54) COMPOUNDS

(71) Applicant: DSM IP ASSETS B.V., Heerlen (NL)

(72) Inventors: Marc Heidl, Kaiseraugst (CH); Eileen Jackson, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 16 days.

(21) Appl. No.: 16/332,506

(22) PCT Filed: Sep. 13, 2017

(86) PCT No.: PCT/EP2017/072952

§ 371 (c)(1),
(2) Date: Mar. 12, 2019

(87) PCT Pub. No.: WO2018/050663

PCT Pub. Date: Mar. 22, 2018

(65) Prior Publication Data

US 2019/0263858 A1 Aug. 29, 2019

(30) Foreign Application Priority Data

Sep. 15, 2016 (EP) .................................... 16188886

(51) Int. Cl.

| | |
|---|---|
| ***C07K 5/083*** | (2006.01) |
| ***C07K 5/097*** | (2006.01) |
| ***C07K 5/08*** | (2006.01) |
| ***A61K 47/54*** | (2017.01) |
| *A61K 8/64* | (2006.01) |
| *A61Q 19/02* | (2006.01) |

(52) U.S. Cl.

CPC .......... *C07K 5/0808* (2013.01); *A61K 47/542* (2017.08); *C07K 5/0804* (2013.01); *C07K 5/0821* (2013.01); *C07K 5/0827* (2013.01); *A61K 8/64* (2013.01); *A61Q 19/02* (2013.01)

(58) Field of Classification Search

None

See application file for complete search history.

(56) References Cited

U.S. PATENT DOCUMENTS 8,431,523 B2 * 4/2013 Owen ..................... A61P 39/06 514/1.1

FOREIGN PATENT DOCUMENTS

WO 2007/039058 4/2007

OTHER PUBLICATIONS

Owen et al., CAS SciFinder abstract (database CASPLUS Acc. No. 2013:679880) of U.S. Pat. No. 8,431,523 (Apr. 30, 2013).*

International Search Report of PCT/EP2017/072952 dated Dec. 4, 2017, 2 pages.

* cited by examiner

*Primary Examiner* — Brian J Davis

(74) *Attorney, Agent, or Firm* — Nixon & Vanderhye P.C.

(57) ABSTRACT

The present invention relates to novel compounds which effectively inhibit the melanin synthesis in human melanocytes and are thus suitable for the treatment of senile lentigines, for smoothening skin color irregularities and/or for lightening natural skin color.

19 Claims, No Drawings

COMPOUNDS

This application is the U.S. national phase of International Application No. PCT/EP2017/072952 filed Sep. 13, 2017 which designated the U.S. and claims priority to EP 16188886.2 filed Sep. 15, 2016, the entire contents of each of which are hereby incorporated by reference.

The present invention relates to novel tripeptides which effectively inhibit the melanin synthesis in human melanocytes and are thus suitable for the treatment of senile lentigines, for smoothening skin color irregularities and/or for lightening natural skin color.

Senile lentigines (also known as senile lentigo or age spots) are hyperpigmented macules of skin that occur in irregular shapes and appear most commonly in the sun-exposed areas of the skin such as on the face and back of the hands. As senile lentigines are a common component of photoaged skin they are quite abundant among elderly people. As the occurrence of senile lentigines, in particular in the face, is often perceived as being aesthetically undesirable, there is a need for cosmetic ingredients which are able to lighten these hyperpigmented macules and thus smoothen the overall skin color.

Tanning is a natural protective function of the skin with varying degrees of distinction in different ethnic groups. In many cultural circles, however, a light skin tone is considered attractive so that a need for lightening the natural skin color arises.

Many ingredients for skin-lightening such as e.g. hydroquinone, kojic acid, arbutin, vitamin C as well as various plant extracts are known. Often, however, significant amounts have to be employed to achieve the desired lightening effect which, in turn, often results in adverse skin reactions such as reddening of the skin or skin rashes.

WO2007039058 discloses the use of opioid receptor antagonists for the manufacture of topical compositions for the suppression of melanin formation in the human skin. WO2007039058, however, does not disclose the use of peptides.

Thus, there is an ongoing need for highly effective and safe skin lightening ingredients which can be used for the treatment of senile lentigines, for smoothening skin color irregularities and/or for lightening the natural skin color.

Surprisingly it has been found that tripeptides of formula (I)

(I)

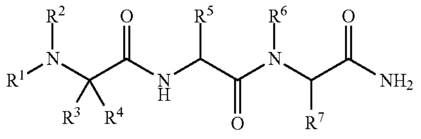

wherein $R^1$ is a $C_9$-$C_{23}$acyl, $R^2$ and $R^3$ are, independently of each other, H or a heteroaryl$C_1$-$C_6$alkyl, wherein the heteroaryl residue may optionally be substituted, $R^4$ is H or a $C_1$-$C_6$alkyl, $R^5$ is an amino acid side chain of a basic amino acid, and $R^6$ and $R^7$ are, independently of each other, selected from the group consisting of H, $C_1$-$C_{12}$alkyl and $C_3$-$C_6$cycloalkyl$C_1$-$C_3$alkyl, or a cosmetically acceptable salt thereof are highly efficient in inhibiting the melanin synthesis in human melanocytes and are thus particularly suitable for the incorporation into cosmetic compositions for the treatment of senile lentigines, for smoothening skin color irregularities and/or for lightening the natural skin color.

Thus, in a first aspect, the present invention relates to a tripeptide of formula (I)

(I)

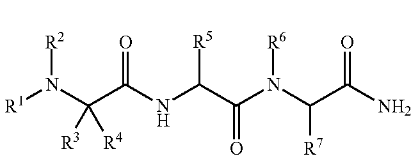

wherein $R^1$ is a $C_9$-$C_{23}$acyl, $R^2$ and $R^3$ are, independently of each other, H or a heteroaryl$C_1$-$C_6$alkyl, wherein the heteroaryl residue may optionally be substituted, $R^4$ is H or a $C_1$-$C_6$alkyl, $R^5$ is an amino acid side chain of a basic amino acid, and $R^6$ and $R^7$ are, independently of each other, selected from the group consisting of H, a $C_1$-$C_{12}$alkyl and a $C_3$-$C_6$cycloalkyl$C_1$-$C_3$alkyl, or a cosmetically acceptable salt thereof.

In all embodiments of the present invention it is preferred that only one of the residues $R^2$ and $R^3$ as well as only one of the residues $R^6$ and $R^7$ is hydrogen (H) and the respective other residue is not hydrogen (H) and/or that at least one of $R^3$, $R^4$ or $R^7$ is not hydrogen (H).

The term '$C_9$-$C_{23}$acyl' refers to —C(═O)$C_8$-$C_{22}$alkyl groups such as nonanoyl ($C_9$), decanoyl ($C_{10}$), undecanoyl ($C_{11}$), dodecanoyl ($C_{12}$), myristoyl ($C_{14}$), palmitoyl ($C_{16}$), stearoyl ($C_{18}$), eicosanoyl ($C_{20}$) and behenoyl ($C_{22}$) as well as —C(═O)$C_8$-$C_{22}$alkenyl groups such as myristoleoyl ($C_{14}$), palmitoleoyl ($C_{16}$), oleoyl ($C_{18}$), linoleoyl ($C_{18}$) and arachidonyl ($C_{20}$). Particularly preferred $C_9$-$C_{23}$acyl groups in all embodiments of the present invention are linear —C(═O)$C_8$-$C_{22}$alkyl groups, preferably linear —C(═O)$C_8$-$C_{19}$alkyl such as in particular nonanoyl, decanoyl, dodecanoyl, myristoyl, palmitoyl, stearoyl and eicosanoyl. Most preferred in all embodiments of the present invention are myristoyl, palmitoyl and stearoyl.

The term 'heteroaryl$C_1$-$C_6$alkyl' refers to a —$C_1$-$C_6$alkyl-heteroaryl group (i.e. to a $C_1$-$C_6$alkyl group which is substituted by a heteroaryl group, i.e. the attachment point is the alkyl group), wherein the term "heteroaryl" refers to a 5- or 6-membered aromatic ring containing one or more heteroatoms, viz., N, O or S; these heteroaromatic rings may be fused to other aromatic systems. Particularly preferred heteroaromatic rings encompass indole, pyridine and quinoline. In all embodiments of the present invention preferred heteroaryl$C_1$-$C_6$alkyl groups are heteroaryl$C_1$-$C_2$alkyl groups such as (1H-indol-3-yl)(m)ethyl, (pyridin-2-yl)(m)ethyl, (pyridin-3-yl)(m)ethyl, (quinolin-2-yl)(m)ethyl and (quinolin-3-yl)(m)ethyl groups.

The aromatic heteroaryl residue in the heteroaryl$C_1$-$C_6$alkyl groups may be unsubstituted or substituted with one or more substituents. Such substituents are preferably selected from halogen, hydroxy, nitro, cyano, $C_1$-$C_6$alkyl, $C_1$-$C_6$alkoxy and $C_1$-$C_6$alkanoyloxy. Preferably, in all embodiments of the present invention, the heteroaryl residues are either unsubstituted or substituted with one substituent selected from the group consisting of F, Cl, hydroxy, cyano, $C_1$-$C_3$alkyl, $C_1$-$C_3$alkoxy and $C_1$-$C_3$alkanoyloxy.

Most preferably, in all embodiments of the present invention, the heteroaryl residues are unsubstituted or substituted with one substituent selected from the group consisting of F or OH. Particular preferred heteroaryl$C_1$-$C_2$alkyl groups for all embodiments of the present invention are (1H-indol-3-yl)(m)ethyl, 5-fluoro(1H-indol-3-yl)(m)ethyl, 6-fluoro(1H-indol-3-yl)(m)ethyl, 5-hydroxy(1H-indol-3-yl)(m)ethyl, (pyridin-2-yl)(m)ethyl, (pyridin-3-yl)(m)ethyl, (quinolin-2-yl)(m)ethyl and (quinolin-3-yl)(m)ethyl, most preferred are (1H-indol-3-yl)methyl, 5-fluoro(1H-indol-3-yl)methyl, 6-fluoro(1H-indol-3-yl)(m)ethyl, 5-hydroxy(1H-indol-3-yl) methyl, (pyridin-2-yl)methyl, (pyridin-3-yl)methyl, (quinolin-2-yl)methyl and (quinolin-3-yl)methyl.

The term '$C_x$-$C_y$alkyl', refers to linear $C_1$-$C_y$alkyl as well as to branched $C_3$-$C_y$alkyl groups such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 2,4,4-trimethylpentyl and 3,5,5-trimethylhexyl groups.

In a preferred embodiment, the $C_1$-$C_6$alkyl for $R^4$ is a $C_1$-$C_2$alkyl, more preferably $CH_3$, the $C_1$-$C_{12}$alkyl for $R^6$ is a branched $C_6$-$C_{10}$ alkyl, more preferably 3,5,5-trimethylhexyl and the $C_1$-$C_{12}$alkyl for $R^7$ is a branched $C_3$-$C_{10}$alkyl, more preferably isobutyl or 2,4,4-trimethylpentyl.

The term "side chain" of an amino acid refers to that portion of the amino acid attached to the common $H_2N$—CH—COOH backbone of the respective amino acids. For instance, the side chain of serine is —$CH_2$—OH and the side chain of alanine is —$CH_3$.

The term "basic amino acid" as used herein refers to any natural or unnatural amino acid that has a basic side chain at neutral pH such as the natural occurring amino acids arginine (Arg), lysine (Lys), and histidine (His) as well as the unnatural amino acids 2,4-diaminobutyric acid, homolysine and ornithine without being limited thereto. Preferred amino acid side chains in all embodiments of the present invention are the side chains of arginine, lysine, diaminobutyric acid, homolysine and ornithine. Most preferred in all embodiments according to the present invention are the side chains of arginine and lysine.

The term '$C_3$-$C_6$cycloalkyl$C_1$-$C_3$alkyl' refers to a saturated, 3 to 6 membered hydrocarbon ring attached to a linear $C_1$-$C_3$alkyl group (i.e. a —$C_1$-$C_3$alkyl$C_3$-$C_6$cycloalkyl group, i.e. a $C_1$-$C_3$alkyl group which is substituted by a cycloalkyl group, i.e. the attachment point is the alkyl group) such as cyclopropyl(m)ethyl, cyclobutyl(m)ethyl, cyclopentyl(m)ethyl, cyclohexyl(m)ethyl. Most preferred in all embodiments according to the present invention the $C_3$-$C_6$cycloalkyl$C_1$-$C_3$alkyl is cyclopropylmethyl.

The term 'or a cosmetically acceptable salt thereof' refers to compounds of formula (I) in the form of an acid addition salt such as in the form of a chloride, an acetate or a trifluoroacetate salt. Alternatively, the salt may be formed by reaction with an alkali or earth alkaline base resulting in the respective alkali or earth alkaline salt such as in particular the respective lithium, sodium, potassium, magnesium or calcium salts. Most preferred, in all embodiments of the present invention, are the compounds of formula (I) as such or in the form of their acetates or trifluoroacetates (i.e. as 2,2,2-trifluoroacetates). Such salts are easily prepared by a person skilled in the art.

Particular advantageous compounds of formula (I) or cosmetically acceptable salts thereof in all embodiments of the present invention are the ones, wherein $R^1$ is a linear —C(═O)$C_8$-$C_{22}$alkyl, preferably a linear —C(═O)$C_8$-$C_{19}$alkyl, more preferably decanoyl, dodecanoyl, myristoyl, palmitoyl, stearoyl and eicosanoyl, most preferably palmitoyl, stearoyl and myristoyl, $R^2$ and $R^3$ are, independently of each other, H or a heteroaryl$C_1$-$C_2$alkyl, preferably H or a heteroarylmethyl, most preferably H or a (1H-indol-3-yl)methyl, (pyridin-2-yl)methyl, (pyridin-3-yl)methyl, (quinolin-2-yl)methyl and (quinolin-3-yl)methyl, wherein the heteroaryl residue is unsubstituted or substituted with one substituent selected from F or OH, $R^4$ is H or a $C_1$-$C_2$alkyl, preferably H or $CH_3$, $R^5$ is an amino acid side chain selected from the side chains of arginine, lysine, diaminobutyric acid, homolysine and ornithine, preferably of arginine and lysine, $R^6$ is H or a branched $C_6$-$C_{10}$alkyl, preferably H or 3,5,5-trimethylhexyl, and $R^7$ is selected from the group consisting of H, a branched $C_3$-$C_{10}$alkyl and a $C_3$-cycloalkyl$C_1$-$C_2$alkyl, preferably from H, isobutyl, 2,4,4-trimethylpentyl and cyclopropylmethyl.

Even more advantageous compounds of formula (I) or cosmetically acceptable salts thereof in all embodiments of the present invention are the ones, wherein $R^1$ is selected from the group consisting of decanoyl, dodecanoyl, myristoyl, palmitoyl, stearoyl and eicosanoyl, $R^2$ and $R^3$ are selected from the group consisting of H, (1H-indol-3-yl)methyl, 5-fluoro(1H-indol-3-yl)methyl, 6-fluoro(1H-indol-3-yl)(m)ethyl, 5-hydroxy(1H-indol-3-yl)methyl, (pyridin-2-yl)methyl, (pyridin-3-yl) methyl, (quinolin-2-yl)methyl and (quinolin-3-yl) methyl, $R^4$ is H or $CH_3$, $R^5$ is the amino acid side chain of arginine or lysine, $R^6$ is H or 3,5,5-trimethylhexyl, and $R^7$ is selected from the group consisting of H, isobutyl, 2,4,4-trimethylpentyl and cyclopropylmethyl, with the proviso that only one of the residues $R^2$ and $R^3$ as well as only one of the residues $R^6$ and $R^7$ is H and the respective other residue is not H.

It is well understood, that the present invention encompasses the compounds of formula (I) as optically pure isomers such as e.g. as pure enantiomers or stereoisomers as well as mixtures of different isomers such as e.g. as racemates, or mixtures of diastereoisomers.

Advantageously, in all embodiments of the present invention the stereocenter 1 is R or S, the stereocenter 2 is S and the stereocenter 3 is S or racemic (mixture of R and S configuration.)

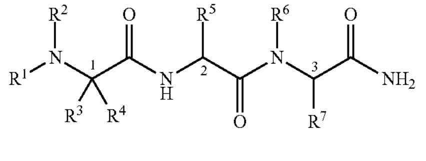

Most preferred in all embodiments according to the present invention are the compounds listed in table 1 as well as the respective trifluoroacetate or acetate salts thereof.

TABLE 1
| # | Structure<br>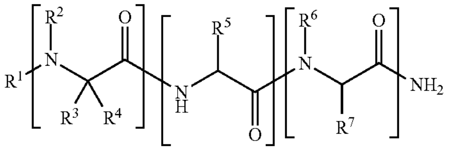<br>AA1 AA2 AA3 | Name<br>$R^1$AA1-AA2-AA3-$NH_2$ |
|---|---|---|
| (I-a) | 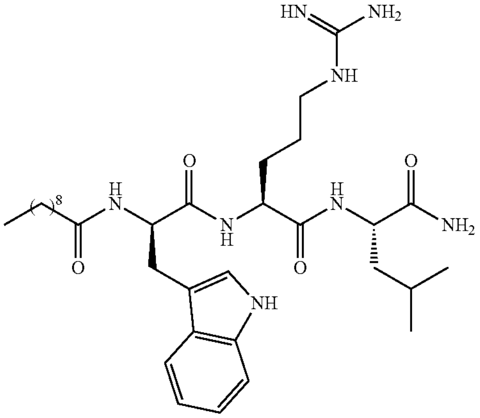 | Decanoyl-D-Trp-Arg-Leu-$NH_2$ |
| (I-b) | 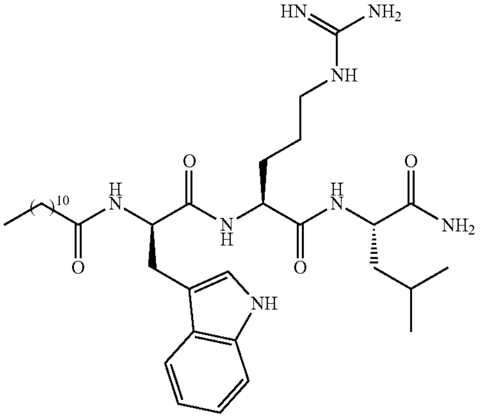 | Lauroyl-D-Trp-Arg-Leu-$NH_2$ |
| (I-c) | 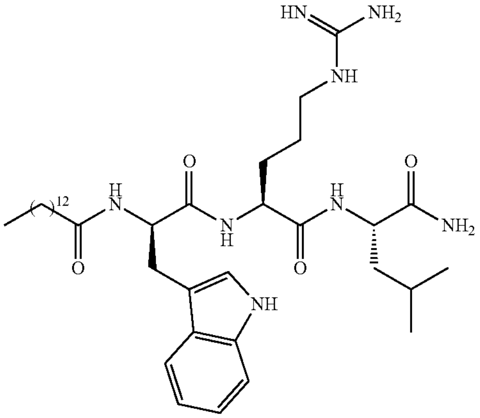 | Myristoyl-D-Trp-Arg-Leu-$NH_2$ |

TABLE 1-continued
| # | Structure<br>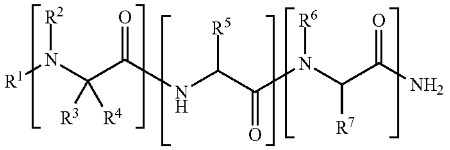<br>AA1 AA2 AA3 | Name<br>$R^1$AA1-AA2-AA3-$NH_2$ |
|---|---|---|
| (I-d) | 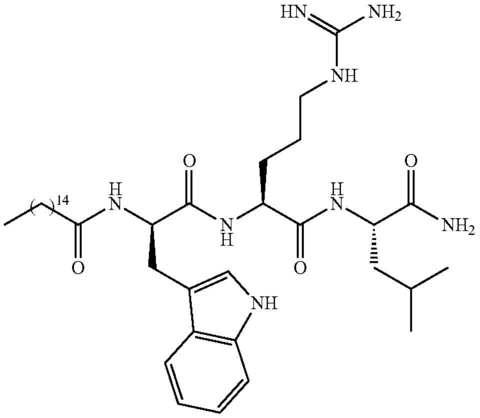 | Palmitoyl-D-Trp-Arg-Leu-$NH_2$ |
| (I-e) | 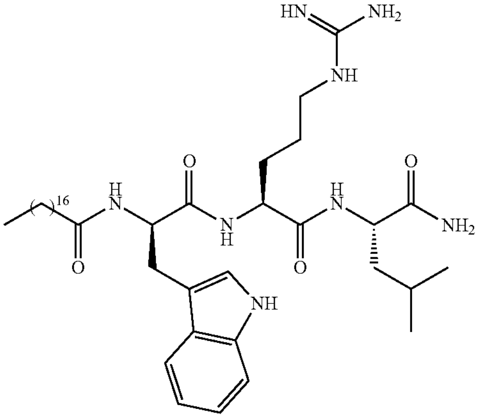 | Stearoyl-D-Trp-Arg-Leu-$NH_2$ |
| (I-f) | 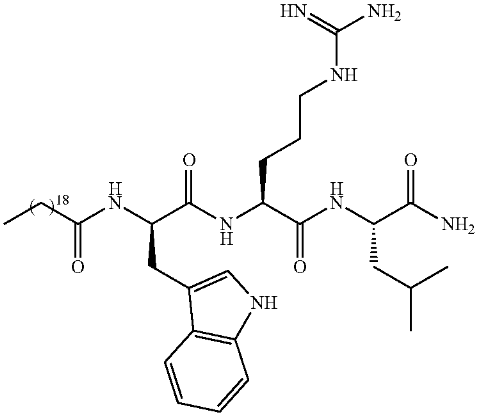 | Eicosanoyl-D-Trp-Arg-Leu-$NH_2$ |

TABLE 1-continued
| # | Structure<br>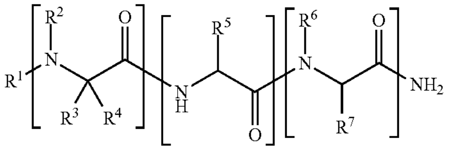<br>AA1 AA2 AA3 | Name<br>$R^1$AA1-AA2-AA3-$NH_2$ |
|---|---|---|
| (I-g) | 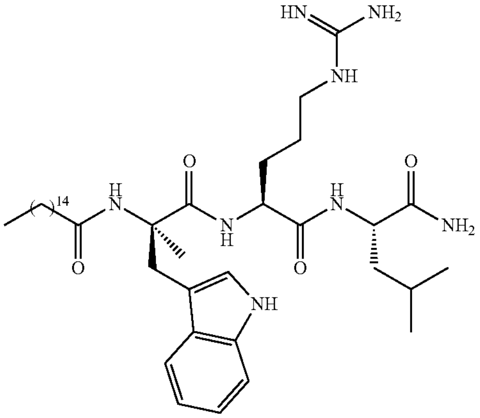 | Palmitoyl-α-Me-D-Trp-Arg-Leu-$NH_2$ |
| (I-h) | 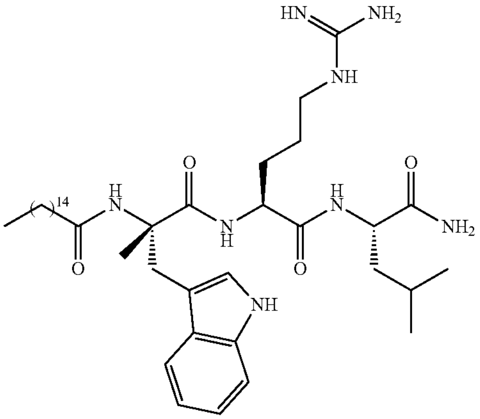 | Palmitoyl-α-Me-L-Trp-Arg-Leu-$NH_2$ |
| (I-i) | 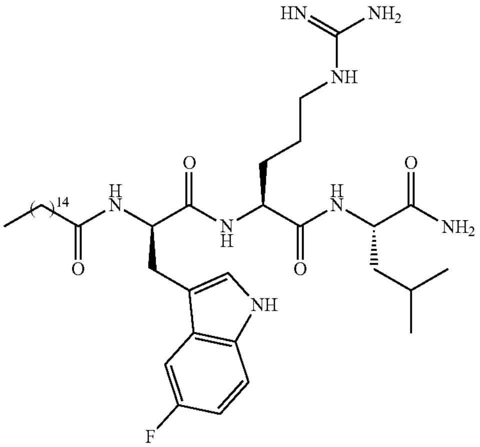 | Palmitoyl-5F-D-Trp-Arg-Leu-$NH_2$ |

TABLE 1-continued
| # | Structure AA1 AA2 AA3 | Name $R^1$AA1-AA2-AA3-$NH_2$ |
|---|---|---|
| | 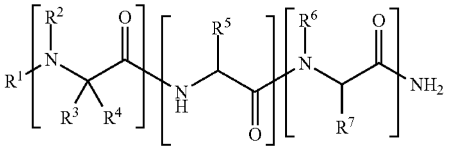 | |
| (I-j) | 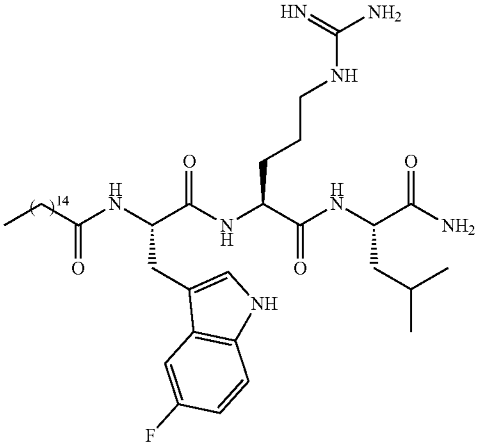 | Palmitoyl-5F-L-Trp-Arg-Leu-$NH_2$ |
| (I-k) | 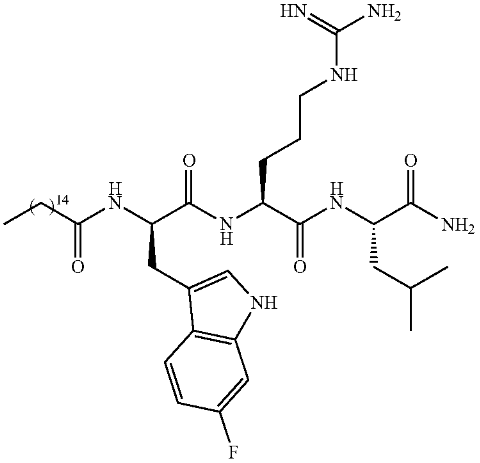 | Palmitoyl-6F-D-Trp-Arg-Leu-$NH_2$ |
| (I-l) | 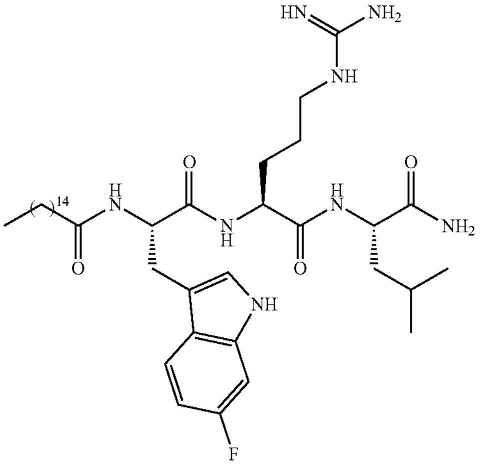 | Palmitoyl-6F-L-Trp-Arg-Leu-$NH_2$ |

TABLE 1-continued
| # | Structure AA1 AA2 AA3 | Name $R^1AA1-AA2-AA3-NH_2$ |
|---|---|---|
| | 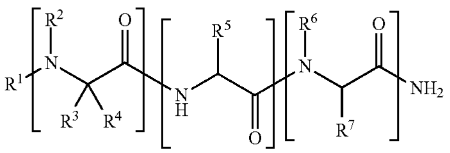 | |
| (I-m) | 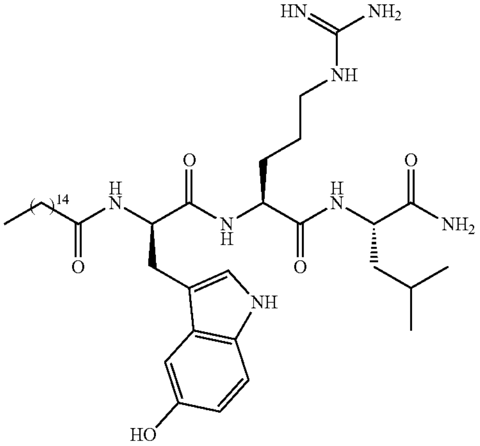 | Palmitoyl-5OH-D-Trp-Arg-Leu-$NH_2$ |
| (I-n) | 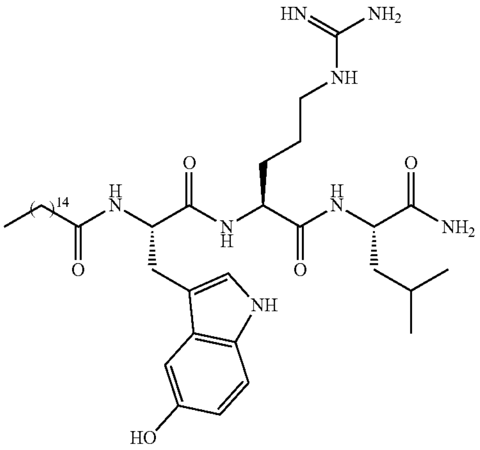 | Palmitoyl-5OH-L-Trp-Arg-Leu-$NH_2$ |
| (I-o) | 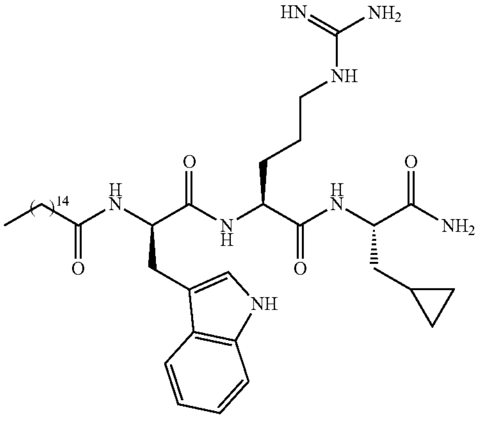 | Palmitoyl-D-Trp-Arg-cyclopropyl-alanin-$NH_2$ |

TABLE 1-continued
| # | Structure<br>AA1 AA2 AA3 | Name<br>$R^1$AA1-AA2-AA3-$NH_2$ |
|---|---|---|
| | 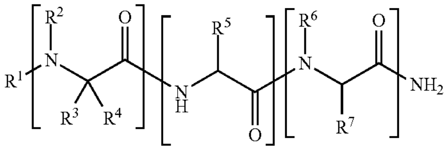 | |
| (I-p) | 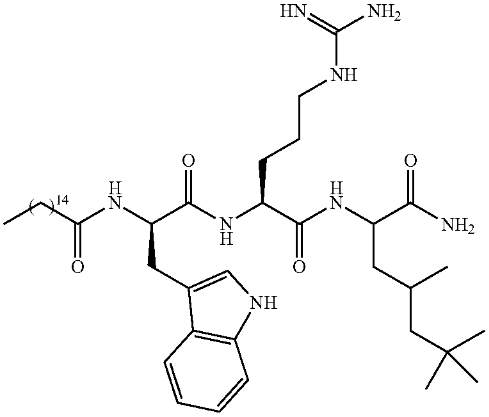 | Palmitoyl-D-Trp-Arg-(all-rac)-2-amino-4,6,6-trimethyl-heptanoic acid-$NH_2$ |
| (I-q) | 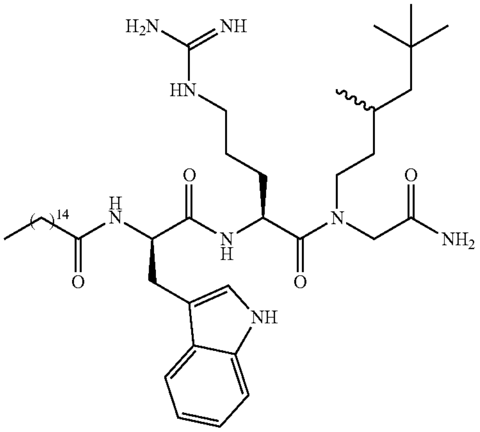 | Palmitoyl-D-Trp-Arg-(rac)-N-3,5,5-trimethylhexylglycin-$NH_2$ |
| (I-r) | 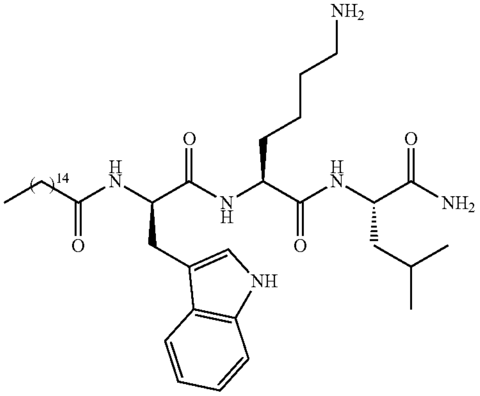 | Palmitoyl-D-Trp-Lys-Leu-$NH_2$ |

TABLE 1-continued
| # | Structure | Name |
|---|---|---|
| | 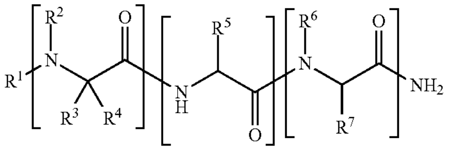 AA1 AA2 AA3 | Name $R^1AA1\text{-}AA2\text{-}AA3\text{-}NH_2$ |
| (I-s) | 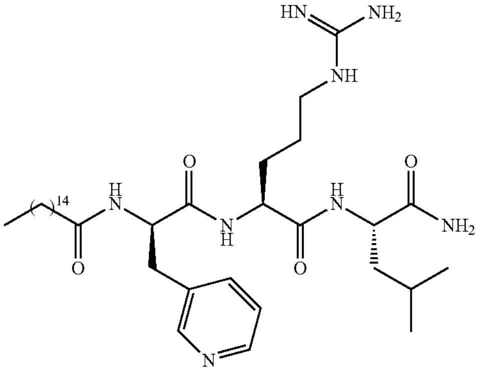 | Palmitoyl-D-3-PyAla-Arg-Leu-$NH_2$ |
| (I-t) | 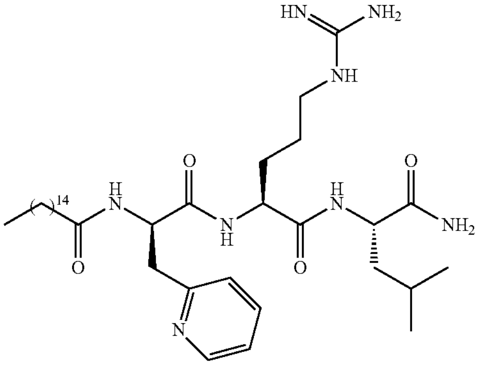 | Palmitoyl-D-2-PyAla-Arg-Leu-$NH_2$ |
| (I-u) | 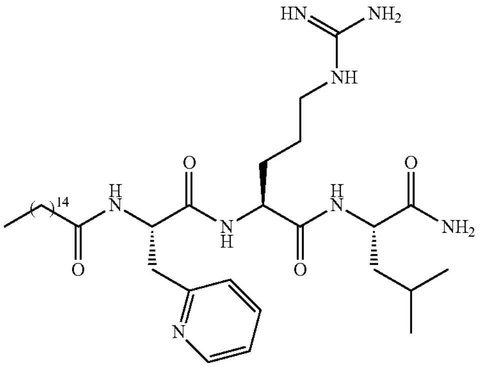 | Palmitoyl-L-2-PyAla-Arg-Leu-$NH_2$ |

TABLE 1-continued

| # | Structure AA1 AA2 AA3 | Name $R^1$AA1-AA2-AA3-$NH_2$ |
|---|---|---|
| | 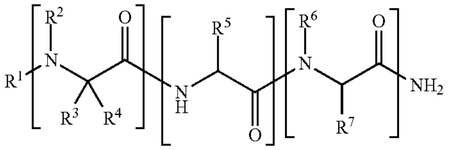 | |
| (I-v) | 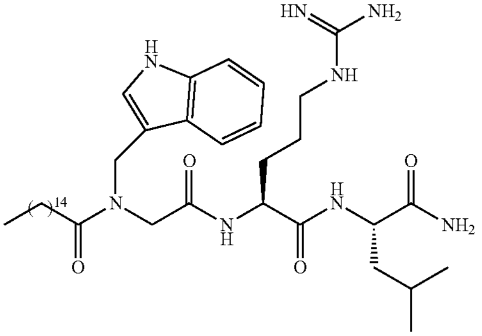 | Palmitoyl-IMGly-Arg-Leu-$NH_2$ |
| (I-w) | 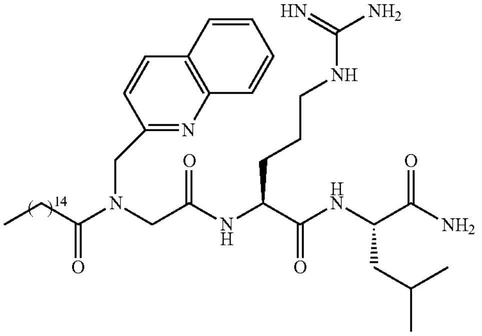 | Palmitoyl-2QMGly-Arg-Leu-$NH_2$ |
| (I-x) | 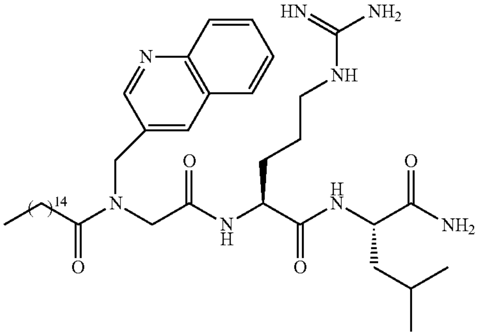 | Palmitoyl-3QMGly-Arg-Leu-$NH_2$ |

The compounds according to the present invention may be prepared by methods standard in peptide using the amino acids AA1, AA2 and AA3 as illustrated in the examples.

In yet another embodiment the present invention relates to the use of a compound of formula (I) with all the definitions and preferences as given herein for the inhibition of the melanin synthesis in human keratinocytes.

Additionally, the invention relates to the cosmetic use of a compound of formula (I) with all the definitions and preferences as given herein for the treatment of senile lentigines, for smoothening skin color irregularities and/or for lightening the natural skin color.

Furthermore, the invention also relates to a cosmetic composition comprising at least one compound of formula (I) with all the definitions and preferences as given herein and a cosmetically acceptable carrier.

The amount of the compound of formula (I) in the cosmetic composition can easily be adjusted by a person skilled in the art in order to achieve the desired beneficial effect.

Preferably, the amount of the compound of formula (I) in the cosmetic compositions according to the present invention is at least 1 ppm based on the total weight of the cosmetic composition. In all embodiments of the present invention the amount of the compound of formula (I) is preferably selected in the range of about 0.00001 to 0.5 wt.-%, more preferably in the range of 0.0001 to 0.25 wt.-%, most preferably in the range of 0.0001 to 0.1 wt.-% based on the total weight of the cosmetic composition.

Furthermore, the invention also relates to a method for the treatment of senile lentigines, for smoothening skin color irregularities and/or for lightening the natural skin color, said method comprising the step of applying a cosmetic composition according to the present invention with all the definitions and preferences given herein to the affected area.

The term 'cosmetic composition' refers to compositions which are used to treat, care for or improve the appearance of the skin and/or the scalp. Particular advantageous cosmetic compositions are skin care compositions.

The cosmetic compositions according to the invention are preferably intended for topical application, which is to be understood as the external application to keratinous substances, such as in particular the skin.

The term 'cosmetically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g., sunscreens, creams, milks, lotions, masks, serums, hydrodispersions, foundations, creams, creamgels, or gels etc.). Such carriers are well-known to one of ordinary skilled in the art, and can include one or more compatible liquid(s) or solid filler diluent(s), excipient(s), additive(s) or vehicle(s) which are suitable for application to skin. The exact amount of carrier will depend upon the level of the compound of formula (I) and any other optional ingredients that one of ordinary skilled in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The cosmetic compositions of the present invention can be formulated into a wide variety of product types, including creams, waxes, pastes, lotions, milks, mousses, gels, oils, tonics, and sprays. Preferably the compounds of formula (I) are formulated into lotions, creams, gels, and tonics. These product forms may be used for a number of applications, including, but not limited to, hand and body lotions, facial moisturizers, anti-ageing preparations, make-ups including foundations, and the like. Any additional components required to formulate such products vary with product type and can be routinely chosen by one skilled in the art.

If compositions of the present invention are formulated as an aerosol and applied to the skin as a spray-on product, a propellant is added to the composition.

The cosmetic compositions according to the present invention can be prepared by conventional methods in the art such as e.g. by admixing a compound of formula (I) with all the definitions and preferences given herein with the cosmetically acceptable carrier. The cosmetic compositions of the invention (including the carrier) may comprise further conventional cosmetic adjuvants and additives, such as preservatives/antioxidants, fatty substances/oils, water, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the cosmetic compositions according to the invention may also comprise further cosmetically active ingredients conventionally used in cosmetic compositions. Exemplary active ingredients encompass further skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Particularly suitable UV-filter to be combined with the compounds of formula (I) according to the present invention encompass all commercially available UV-filter substances such as (INCI names) polysilicones-15, phenylbenzimidazol sulfonic acid, 3-benzylidene camphor, octocrylene, ethylhexyl methoxycinnamate, ethyl hexylsalicylate, homosalate, ethylhexyl triazone, zinc oxide, bis-ethylhexyloxyphenol methoxyphenyl triazine, diethylhexyl butamido triazone, tris biphenyl triazine, benzophenon-3, methylene bis-benzotriazolyl tetramethylbutylphenol, titanium dioxide, butyl methoxydibenzoylmethane, disodium phenyl dibenzimidazole tetrasulfonate and diethylamino hydroxybenzoyl hexyl benzoate without being limited thereto.

Preferred UV-filters to be combined with the compounds of formula (I) according to the present invention are (INCI names/trade names) polysilicones-15 (PARSOL® SLX), phenylbenzimidazol sulfonic acid (PARSOL® HS), 3-benzylidene camphor (PARSOL® 5000), octocrylene (PARSOL® 340), ethylhexyl methoxycinnamate (PARSOL® MCX), ethyl hexylsalicylate (PARSOL® EHS), homosalate (PARSOL® HMS), zinc oxide, bis-ethylhexyloxyphenol methoxyphenyl triazine (PARSOL® SHIELD), methylene bis-benzotriazolyl tetramethylbutylphenol (PARSOL® MAX), titanium dioxide (e.g. PARSOL® TX) and butyl methoxydibenzoylmethane (PARSOL® 1789) as well as mixtures thereof.

Particularly suitable skin lightening ingredients to combined with the compounds of formula (I) according to the present invention encompass niacinamide, arbutin such as in particular alpha-arbutin, resveratrol, vitamin C (ascorbic acid) as well as derivatives thereof such as in particular sodium and/or magnesium ascorbyl phosphate, (skin whitening) plant extracts such as in particular Malva *Sylvestris* (Mallow) Flower/Leaf/Stem Extract, *Mentha Piperita* (Peppermint) Leaf Extract, *Primula* Veris Flower Extract, Alchemilla Vulgaris Flower/Leaf/Stem Extract, *Veronica Officinalis* Flower/Leaf/Stem Extract, *Melissa Officinalis* Leaf Extract, *Achillea Millefolium* Flower/Leaf/Stem Extract, Thymus Hydrolysate as well as mixtures thereof. Such products are e.g. commercially available from DSM Nutritional Products Ltd. under the tradenames Alpaflor® Gigawhite, Melawhite® PF, Melfade® PF, REGU®-FADE, NIACINAMIDE PC, STAY-C® 50, Biotin, Radiance CR, Retinol GS 50.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients can in some instances provide more than one benefit or operate via more than one mode of action.

Of course, one skilled in this art will take care to select the above mentioned optional additional ingredients, adjuvants, diluents and additives and/or their amounts such that the advantageous properties associated with the combination in accordance with the invention are not, or not substantially, detrimentally affected by the envisaged addition or additions.

The cosmetic compositions according to the present invention may be in the form of a suspension or dispersion in solvents or fatty substances, or alternatively in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the cosmetic composition is an emulsion, such as in particular an O/W, W/O, Si/W, W/Si, O/W/O, W/O/W multiple or a pickering emulsion, then the amount of the oily phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the cosmetic composition.

In one embodiment, the cosmetic compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the cosmetic composition according to the invention is an O/W emulsion, then it contains advantageously at least one O/W- or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the cosmetic composition.

Particular suitable O/W emulsifiers to be used in the cosmetic compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

A particular suitable O/W emulsifier to be used in the cosmetic compositions according to the invention is potassium cetyl phosphate e.g. commercially available as Amphisol® K at DSM Nutritional Products Ltd Kaiseraugst.

Another particular suitable class of O/W emulsifiers are non-ionic self-emulsifying systems derived from olive oil e.g. known as (INCI Name) cetearyl olivate and sorbitan olivate (chemical composition: sorbitan ester and cetearyl ester of olive oil fatty acids) sold under the tradename OLIVEM 1000.

In one particular embodiment, the invention relates to cosmetic compositions with all the definitions and preferences given herein in the form of O/W emulsions comprising an oily phase dispersed in an aqueous phase in the presence of an O/W emulsifier wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%, based on the total weight of the composition.

The cosmetic compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The amount of the cosmetic composition to be applied to the skin is not critical and can easily be adjusted by a person skilled in the art. Preferably the amount is selected in the range of 0.1 to 3 $mg/cm^2$ skin, such as preferably in the range of 0.1 to 2 $mg/cm^2$ skin and most preferably in the range of 0.5 to 2 $mg/cm^2$ skin.

The invention is further illustrated with reference to the following, non-limiting examples, in which all percentages are by weight based on total weight unless otherwise specified.

EXPERIMENTAL PART

1. General Information

Abbreviations

AA Amino acid
ATMPA (all-rac) 2-amino-2,6,10,14-tetramethyl pentadecanoic acid
DCM dichloromethane
DIPE diisopropylether
DIPEA N,N-diisopropylethylamine
EtOAc ethyl acetate
Fmoc fluorenylmethoxycarbonyl
HOAc acetic acid
HPLC High Pressure Liquid Chromatography
MeCN acetonitrile
TIPS triisopropylsilane?
TFA trifluoroacetic acid
TBTU O-(Benzotriazol-1-yl)-N,N,N',N'-tetramethyluronium tetrafluoroborat
2PyAla 3-(2-Pyridyl)-alanine 3PyAla 3-(3-Pyridyl)-alanine
IMGly N-(1H-indoly-3-yl methyl)glycine
3QMGly N-(quinolin-3-yl methyl)glycine
2QMGly N-(quinolin-2-yl methyl)glycine Preparative HPLC Purifications: Performed on a Waters High Performance Liquid Chromatography LC-2525 equipped with a Waters 2767 Sample Manager and a Waters FCII automated fraction collector, using a Grom Saphir 110 C18 10 μm 50×300 mm² preparative column and a Waters 2487 double wavelength UV-Vis detector operating at 220 and 254 nm.

$H_2O$+0.07% TFA (A" phase) and MeCN+0.07% TFA (B" phase) were used as eluents, with a flow of 55 mL/min.

Synthetic Strategies

All compounds are prepared using a commercially available peptide synthesizer to prepare the tripeptide with free N-terminus or N-terminal fatty acid. In cases where the desired single stereoisomer was not commercially available, the racemic mixture was coupled to the side-chain protected dipeptide on the resin and the epimers were separated by preparative HPLC.

Procedure 0: Typical Synthesis of the Precursor: H-AA1-AA2-AA3-NH-Resin 1.4 g of Fmoc ramage amide polystyrene resin (approx. 0.51 mmol/g) is swollen in DCM for 2 h in a peptide synthesizer reaction vessel. The peptide synthesizer runs the synthesis program for tripeptides using 1.25 equivalents of each Fmoc-protected amino acid. Expensive or home-made amino acids can be used as limiting reagent followed by acetylation of excess of unreacted amine.

Procedure 1: Free Peptide:

1.5 mmoles of Fmoc ramage resin were treated as described in the precursor procedure, then cleaved from the resin with 30 ml 95% TFA and precipitated with 350 ml DIPE. The crude peptide is filtered off, dried, treated 30 mins with 2N HOAc and purified with preparative HPLC. Pure fractions are combined, evaporated and dried at the lyophilizer yielding the peptides as outlined in Table 2a.

TABLE 2a

| # | Name | Yield |
|---|---|---|
| Ref-5 | H-D-Trp-Arg-Leu-NH$_2$ *2TFA | 673 mg, 0.95 mmol, 63% |

Procedure 2: Desired Stereoisomer Commercially Available or all-Rac Mixture 1.0-1.5 mmoles of Fmoc ramage resin were treated as described in the previous procedure. The N-terminal fatty acid is coupled via standard peptide coupling procedure. The crude peptide is then cleaved from the resin with 30 ml 95% TFA and precipitated with 350 ml DIPE. The crude peptide is filtered off, dried, treated 30 mins with 2N HOAc and purified by preparative HPLC. Pure fractions are combined, evaporated and dried onat the lyophilizer yielding the peptides as outlined in Table 2b TABLE 2b

| # | Name | Yield |
|---|---|---|
| (I-a) | Decanoyl-D-Trp-Arg-Leu-NH$_2$ *TFA | 353 mg, 0.47 mmol, 64% |
| (I-b) | Lauroyl-D-Trp-Arg-Leu-NH$_2$ *TFA | 310 mg, 0.40 mmol, 40% |
| (I-c) | Myristoyl-D-Trp-Arg-Leu-NH$_2$ *TFA | 203 mg, 0.25 mmol, 25% |
| (I-d) | Palmitoyl-D-Trp-Arg-Leu-NH$_2$ *TFA | 236 mg, 0.28 mmol, 22% |
| (I-e) | Stearoyl-D-Trp-Arg-Leu-NH$_2$ *TFA | 45 mg, 0.05 mmol, 5% |
| (I-f) | Eicosanoyl-D-Trp-Arg-Leu-NH$_2$ *TFA | 74 mg, 0.08 mmol, 11% |
| (I-o) | Palmitoyl-D-Trp-Arg-cyclopropyl-alanin-NH$_2$ *TFA | 125 mg, 0.14 mmol, 69% |
| (I-p) | Palmitoyl-D-Trp-Arg-(all-rac)-2-amino-4,6,6-trimethyl-heptanoic acid-NH$_2$ *TFA | 172 mg, 0.19 mmol, 24% |
| (I-q) | Palmitoyl-D-Trp-Arg-(rac)-N-3,5,5-trimethylhexylglycin-NH$_2$ *TFA | 112 mg, 0.12 mmol, 12% |
| (I-r) | Palmitoyl-D-Trp-Lys-Leu-NH$_2$ *TFA | 387 mg, 0.48 mmol, 48% |
| (I-s) | Palmitoyl-D-3-PyAla-Arg-Leu-NH$_2$ *2TFA | 155 mg, 0.16 mmol, 51% |
| (I-w) | Palmitoyl-2QMGly-Arg-Leu-NH2 *2TFA | 67 mg, 0.06 mmol, 13% |
| (I-x) | Palmitoyl-3QMGly-Arg-Leu-NH2 *TFA | 225 mg, 0.23 mmol, 47% |
| Ref-1 | Palmitoyl-D-Trp-Met-Leu-NH2 | 249 mg, 0.36 mmol, 36% |
| Ref-2 | Hexanoyl-D-Trp-Arg-Leu-NH2 *2TFA | 72 mg, 0.10 mmol, 8% |
| Ref-3 | Palmitoyl-D-Trp-NLe-Leu-NH2 | 39 mg, 0.06 mmol, 6% |
| Ref-4 | Octanoyl-D-Trp-Arg-Leu-NH2 *TFA | 306 mg, 0.43 mmol, 43% |
| Ref-6 | Palmitoyl-D-Trp-Arg-ATMPA-NH2 *2TFA | 110 mg, 0.17 mmol, 17% |

Procedure 3: Synthesis Via Separation of Epimers 1.0-1.5 mmoles of Fmoc ramage resin were treated as described in the previous procedure. The crude peptide is then cleaved from the resin with 30 ml of 95% TFA and precipitated with 350 ml DIPE. The crude peptide is filtered off, dried, treated 30 mins with 2N HOAc and purified by preparative HPLC. By comparison, we concluded the D-epimer elutes first in the (rac)Trp-derivative-Arg-Leu-NH$_2$ series. The N-terminal palmitic acid is coupled via standard peptide coupling procedure using 1.2 eq of TBTU and palmitic acid and 4.5 eq DIPEA. After final preparative HPLC, the pure fractions are combined, evaporated and dried at the lyophilizer yielding the peptides as outlined in Table 2c.

TABLE 2c

| # | Name | Yield |
|---|---|---|
| (I-g) | Palmitoyl-α-Me-D-Trp-Arg-Leu-NH$_2$ *TFA | 92 mg, 0.11 mmol, 50% |
| (I-h) | Palmitoyl-α-Me-L-Trp-Arg-Leu-NH$_2$ *TFA | 72 mg, 0.14 mmol, 58%) |
| (I-i) | Palmitoyl-5F-D-Trp-Arg-Leu-NH$_2$ *TFA | 92 mg, 0.11 mmol, 52% |
| (I-j) | Palmitoyl-5F-L-Trp-Arg-Leu-NH$_2$ *TFA | 101 mg, 0.21 mmol, 57% |
| (I-k) | Palmitoyl-6F-D-Trp-Arg-Leu-NH$_2$ *TFA | 108 mg, 0.13 mmol, 61% |
| (I-l) | Palmitoyl-6F-LTrp-Arg-Leu-NH$_2$ *TFA | 103 mg, 0.12 mmol, 58% |
| (I-m) | Palmitoyl-5OH-D-Trp-Arg-Leu-NH$_2$ *TFA | 83 mg, 0.10 mmol, 48% |
| (I-n) | Palmitoyl-5OH-L-Trp-Arg-Leu-NH$_2$ *TFA | 95 mg, 0.11 mmol, 53% |

TABLE 2c-continued

| | Name | Yield |
|---|---|---|
| (I-t) | Palmitoyl-D-2-PyAla-Arg-Leu-$NH_2$ *2TFA | 61 mg, 0.17 mmol, 41%) |
| (I-u) | Palmitoyl-L-2-PyAla-Arg-Leu-$NH_2$ *2TFA | 41 mg, 0.10 mmol, 46% |

Procedure 4: Compounds Requiring Special Treatment 1.5 mmoles of Fmoc ramage resin were treated as described in the precursor procedure, then cleaved from the resin with 25.8 ml (TFA/TIPS/DCM=22/0.8/3 ml) saturated with dry ice. The cleavage mixture was added dropwise to an ice-cooled mixture of 100 ml water and 120 ml of 1M NaOH and adjusted to a pH=8 with additional NaOH. The mixture is evaporated to a volume of approx. 200 ml, and directly feed into prep. HPLC using HOAc as modifier for Water and MeCN. Pure fractions are neutralized, combined and extracted with EtOAc. Organic layer is dried with $Na_2SO_4$, and all volatile compounds are removed under reduced pressure.

The N-terminal palmitic acid was coupled via standard peptide coupling procedure using 1.1 eq of TBTU and palmitic acid and 3 eq DIPEA yielding the peptide as outlined in Table 2d.

TABLE 2d

| | Name | Yield |
|---|---|---|
| (I-v) | Palmitoyl-IMGly-Arg-Leu-$NH_2$ *AcOH | 5 mg, 0.001 mmol, 5% |

3. Melanin Inhibition

Melanocytes (Normal human epidermal melanocytes, lightly pigmented, $8^{th}$ passage) were seeded in 24 well plates and cultured for 24 hours in culture medium (M254 supplemented with PMA free HMGS-2, Insulin 5 µg/ml, Penicilline 50 U/ml-Streptomycine 50 µg/ml Gentamycine 25 µg/ml) at 37° C., 5% $CO_2$. The medium was then replaced by culture medium containing the test compounds or the reference (lipoic acid at 5 µg/ml) in presence of L-tyrosine (1 mM). The cells were then incubated for 240 hours with 2 renewals of culture medium containing the test compounds or the reference in presence of L-tyrosine after 96 and 168 hours of incubation. A non-stimulated and a stimulated control were performed in parallel. All experimental conditions were performed in n=3, except for control conditions in n=6. At the end of incubation, the culture supernatants were removed and the melanin was extracted by cell lysis using a 0.5 N NaOH solution. The optical density (OD) of each experimental point was measured at 405 nm and melanin quantity was calculated using melanin standards (standard curve from 0.39 to 100 µg/ml melanin). Results were expressed in µg/ml of melanin and in percentage of inhibition compared to stimulated control.

| | | Melanin inhibition [%] | |
|---|---|---|---|
| # | Name | 1 µM | 10 µM |
| (I-a) | Decanoyl-D-Trp-Arg-Leu-$NH_2$ *TFA | na | 75 |
| (I-b) | Lauroyl-D-Trp-Arg-Leu-NH2 *TFA | 51 | 73 |
| (I-c) | Myristoyl-D-Trp-Arg-Leu-$NH_2$ *TFA | 62 | 70 |
| (I-d) | Palmitoyl-D-Trp-Arg-Leu-$NH_2$ *TFA | 76 | na |
| (I-e) | Stearoyl-D-Trp-Arg-Leu-$NH_2$ *TFA | 66 | 64 |
| (I-f) | Eicosanoyl-D-Trp-Arg-Leu-$NH_2$ *TFA | 28 | 55 |
| (I-g) | Palmitoyl-α-Me-D-Trp-Arg-Leu-NH2 *TFA | 94 | na |
| (I-h) | Palmitoyl-α-Me-L-Trp-Arg-Leu-NH2 *TFA | 70 | na |
| (I-i) | Palmitoyl-5F-D-Trp-Arg-Leu-NH2 *TFA | 77 | na |
| (I-j) | Palmitoyl-5F-L-Trp-Arg-Leu-NH2 *TFA | 60 | na |
| (I-k) | Palmitoyl-6F-D-Trp-Arg-Leu-NH2 *TFA | 70 | na |
| (I-l) | Palmitoyl-6F-L-Trp-Arg-Leu-NH2 *TFA | 59 | na |
| (I-m) | Palmitoyl-5OH-D-Trp-Arg-Leu-$NH_2$ *TFA | 75 | na |
| (I-n) | Palmitoyl-5OH-L-Trp-Arg-Leu-$NH_2$ *TFA | 42 | na |
| (I-o) | Palmitoyl-D-Trp-Arg-cyclopropyl-alanin-$NH_2$ *TFA | 65 | 65 |
| (I-p) | Palmitoyl-D-Trp-Arg-(all-rac)-2-amino-4,6,6-trimethyl-heptanoic acid-$NH_2$ *TFA | 71 | na |
| (I-q) | Palmitoyl-D-Trp-Arg-(rac)-N-3,5,5-trimethylhexylglycin-$NH_2$ *TFA | 73 | na |
| (I-r) | Palmitoyl-D-Trp-Lys-Leu-$NH_2$ *TFA | 61 | na |
| (I-s) | Palmitoyl-D-3-Py-Ala-Arg-Leu-$NH_2$ *2TFA | 64 | 75 |
| (I-t) | Palmitoyl-D-2-PyAla-Arg-Leu-$NH_2$ *2TFA | 59 | na |
| (I-u) | Palmitoyl-L-2-PyAla-Arg-Leu-$NH_2$ *2TFA | 32 | na |
| (I-v) | Palmitoyl-IMGly-Arg-Leu-$NH_2$ *AcOH | 58 | na |
| (I-w) | Palmitoyl-2QAla-Arg-Leu-$NH_2$ *2TFA | 58 | na |
| (I-x) | Palmitoyl-3QAla-Arg-Leu-$NH_2$ *TFA | 65 | na |

2. References (Comparative Example)

Various reference compounds (see above Ref-x compounds) have been prepared and tested in the melanogenese assay. As can be retrieved from table 3, these compounds showed only little or no activity at all (at 1 µM concentration). Some of the reference compounds even increased the melanin content in the human melanocytes, thus exhibited a tanning effect.

TABLE 3

| | | Melanin inhibition [%] | |
|---|---|---|---|
| # | Name | 1 µM | 10 µM |
| Ref-1 | Palmitoyl-D-Trp-Met-Leu-$NH_2$ | 25 | 43 |
| Ref-2 | Hexanoyl-D-Trp-Arg-Leu-$NH_2$ | 18 | 8 |
| Ref-3 | Palmitoyl-D-Trp-NLe-Leu-$NH_2$ | 13 | na |
| Ref-4 | Octanoyl-D-Trp-Arg-Leu-$NH_2$ | 13 | na |
| Ref-5 | H-D-Trp-Arg-Leu-$NH_2$ | −3 | 14 |
| Ref-6 | Palmitoyl-D-Trp-Arg-ATMPA-$NH_2$ | −3 | −12 |

3. Cosmetic Composition

Table 4 outlines exemplary O/W emulsions, wherein one compound selected from the group of (I-a) to (I-x) as outlined in table 1 is incorporated in the indicated amount.

TABLE 4

| | Exemplary O/W emulsion | | | | | | | |
|---|---|---|---|---|---|---|---|---|
| O/W Emulsions | 1 | 2 | 3 | 4 | 5 | 6 | 7 | 8 |
| Glyceryl Stearate | 2.5 | 2 | 1.2 | 1 | | | 1 | 1 |
| PEG-40 Stearate | 1 | | | | | | | |
| PEG-100 Stearate | | 2.5 | | | | | | 1 |
| Ceteareth-20 | | | | | 1 | | | |
| Glyceryl Stearate Citrate | | | | | | 0.5 | | |
| Potassium Cetyl Phosphate | | | | | | | 3 | 1.5 |
| Stearic Acid | | | 2.5 | 3 | | | | |
| Cetearyl Alcohol | 4 | | | 2 | | | 2 | |
| Stearyl Alcohol | | 2 | 1 | | | | | |
| Cetyl Alcohol | | | 1 | 1 | | | | 0.5 |
| Acrylates/$C_{10-30}$ Alkyl Acrylate Crosspolymer | | | | 0.2 | 0.2 | 0.4 | 0.2 | |
| Carbomer | 0.1 | | 0.2 | | | | | |
| Xanthan Gum | | 0.3 | | | | | | 0.3 |
| $C_{12-15}$ Alkyl Benzoate | 5 | | | 2 | 5 | 5 | 10 | 5 |
| Petrolatum | 5 | | 3 | | | | | |
| Butylene Glycol Dicaprylate/Dicaprate | | 4 | 2 | | 9 | | | 9 |
| Hydrogenated Polydecene | | | 3 | | 2 | | | 2 |
| Caprylic/Capric Triglyceride | 1 | 3 | | 5 | | 5 | 5 | |
| Cyclomethicone | | 5 | 2 | | | 10 | | |
| Methylpropanediol | 2 | | | | 3 | | | 3 |
| Glycerine | 4 | 7 | 3 | 4 | 3 | | 5 | 3 |
| Glyceryl Glucoside | 3.5 | 3 | 1 | 1 | 2 | | | 2 |
| Alcohol denat. | 1 | 3 | 0.5 | 10 | 4 | 8 | | 4 |
| Butylene Glycol | | | 3 | | | | | |
| Ascorbylglucoside | | 0.5 | | 1.0 | | 1.5 | | 0.1 |
| Ubiquinone (Coenzyme 10) | 0.1 | | 0.05 | | | | 0.01 | |
| Hyaluronic acid | | | | | 0.2 | | | |
| Bisabolol | 0.5 | | | | | | 0.2 | |
| Isotridecylsalicylate | | | 1 | 3 | 5 | 2 | 3 | 5 |
| Compound selected from the group of (I-a) to (I-x) | 0.001 | 0.25 | 0.0001 | 0.05 | 0.1 | 0.0003 | 0.03 | 0.002 |
| Dibutyl Adipate | 1.5 | 3 | | | | | | |
| Diisopropyl sebacate | | 1 | 1 | 2 | 3 | | | |
| Ethylhexyl Benzoate | | | | | | 0.75 | 1.5 | 1 |
| Titanium Dioxide (PARSOL TX) | | | 0.5 | 2 | | | | |
| Methylene Bis-Benztriazoyl Tetramethylbutylphenol | | | 0.5 | 4 | | 6 | | 2 |
| Ethylhexyl methoxycinnamate | | | | | 2 | | | |
| Phenylbenzimidazole Sulfonic Acid | | | | 2 | | 2 | 2 | |
| Butyl Methoxydibenzoylmethane | | 1 | | 2 | 2 | 3 | 3 | 3 |
| Methylbenzylidene Camphor | | | | | 2 | 3 | | |
| Octocrylene | | 5 | | | | 2 | 10 | |
| Polysilicone-15 | | | | 2 | | 3 | | |
| Ethylhexyl Salicylate | | | | | 5 | | | |
| Homosalate | | | 4 | | 2 | | | |
| Bis-Ethylhexyloxyphenol Methoxyphenyltriazine | | 1.5 | | | | | | 2 |
| Silica | 1 | | 2.5 | | | 0.5 | | |
| Silica & Methicone | | 4 | | 1 | 2.5 | | | |
| Methyl Methacrylate Crosspolymer | | | | 1 | | | 2 | |
| Disodium EDTA | 0.1 | | | | | 0.5 | | |
| Fragrance, Preservatives | | | | q.s. | | | | |
| Sodium Hydroxide | | | | q.s. | | | | |
| Water | | | | Ad 100 | | | | |

The invention claimed is:

1. A compound of formula (I):

(I)

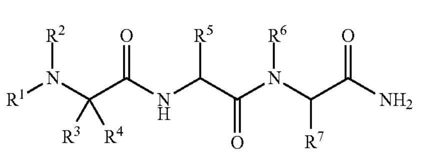

wherein $R^1$ is a $C_9$-$C_{23}$acyl, $R^2$ and $R^3$ are, independently of each other, H or a heteroaryl$C_1$-$C_6$alkyl, wherein the heteroaryl residue may optionally be substituted, $R^4$ is H or a $C_1$-$C_6$alkyl, $R^5$ is an amino acid side chain of a basic amino acid, and $R^6$ and $R^7$ are, independently of each other, selected from the group consisting of H, a $C_1$-$C_{12}$alkyl and a $C_3$-$C_6$cycloalkyl$C_1$-$C_3$alkyl or a cosmetically acceptable salt thereof, with the proviso that only one of the residues $R^2$ and $R^3$ as well as only one of the residues $R^6$ and $R^7$ is H and/or at least one of $R^3$, $R^4$ or $R^7$ is not H.

2. The compound according to claim 1, wherein the $C_9$-$C_{23}$acyl is selected from the group consisting of nonanoyl, decanoyl, undecanoyl, dodecanoyl, myristoyl, palmitoyl, stearoyl and eicosanyl.

3. The compound according to claim 1, wherein the heteroaryl$C_1$-$C_6$alkyl is unsubstituted or substituted with one substituent selected from the group consisting of F, CI, hydroxy, cyano, $C_1$-$C_3$alkyl, $C_1$-$C_3$alkoxy and $C_1$-$C_3$alkanoyloxy.

4. The compound according to claim 3, wherein the heteroaryl$C_1$-$C_6$alkyl is selected from the group consisting of (1 H-indol-3-yl)(m)ethyl, 5-fluoro(1 H-indol-3-yl)(m) ethyl, 6-fluoro(1 H-indol-3-yl)(m)ethyl, 5-hydroxy(1 H-indol-3-yl)(m)ethyl, (pyridin-2-yl)(m)ethyl, (pyridin-3-yl)(m) ethyl, (quinolin-2-yl)(m)ethyl and (quinolin-3-yl)(m)ethyl.

5. The compound according to claim 1, wherein $R^4$ is H or a $C_1$-$C_2$alkyl.

6. The compound according to claim 1, wherein the amino acid side chain is selected from the side chains of arginine, lysine, and histidine, 2,4-diaminobutyric acid, homolysine and ornithine.

7. The compound according to claim 1, wherein $R^6$ is H or a branched $C_6$-$C_{10}$alkyl.

8. The compound according to claim 1, wherein $R^7$ is selected from the group consisting of H, a branched $C_3$-$C_{10}$alkyl and a $C_3$-cycloalkyl$C_1$-$C_2$alkyl.

9. The compound according to claim 1, which is a compound of one of the formulas (I-a) through (I-x):

(I-a)

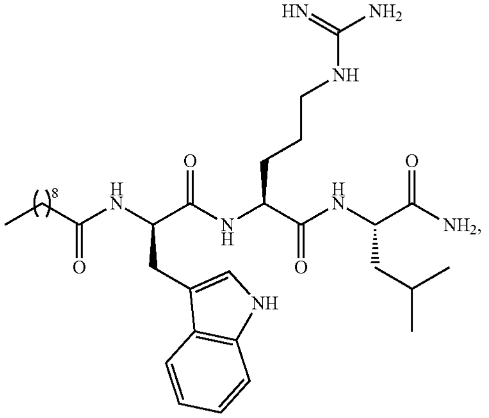

(I-b)

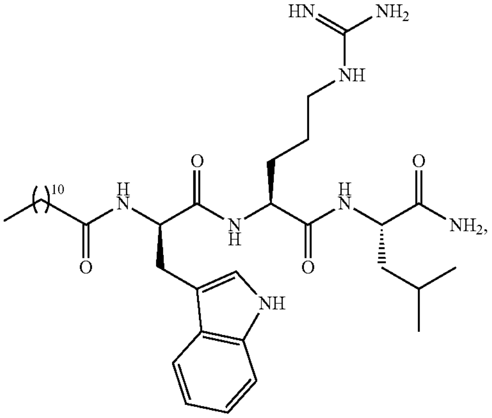

-continued (I-c)

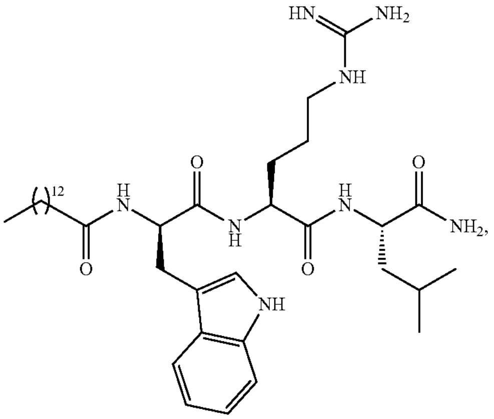

(I-d)

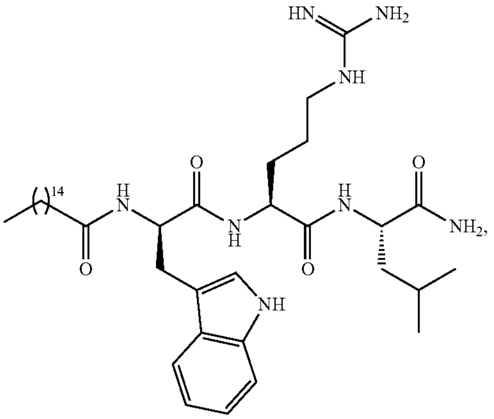

(I-e)

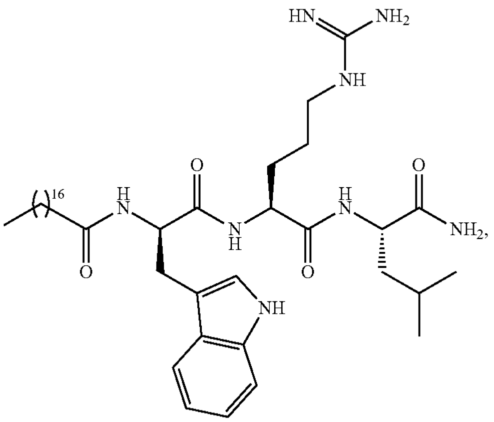

-continued
(I-f)
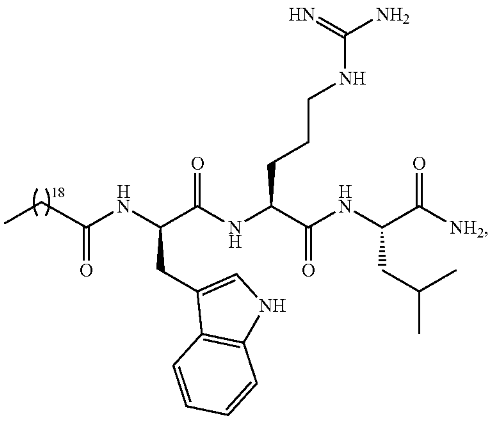
(I-g)
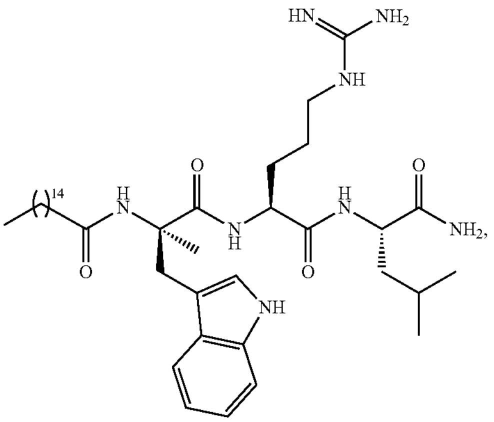
(I-h)
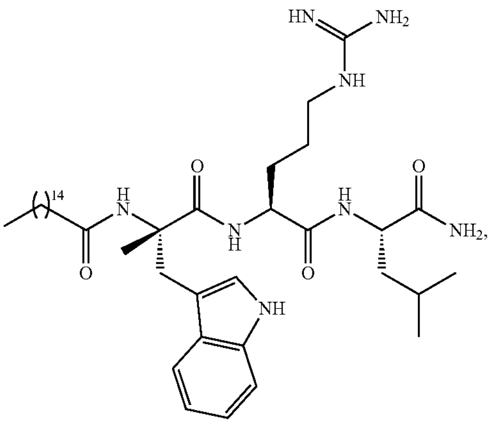
-continued
(I-i)
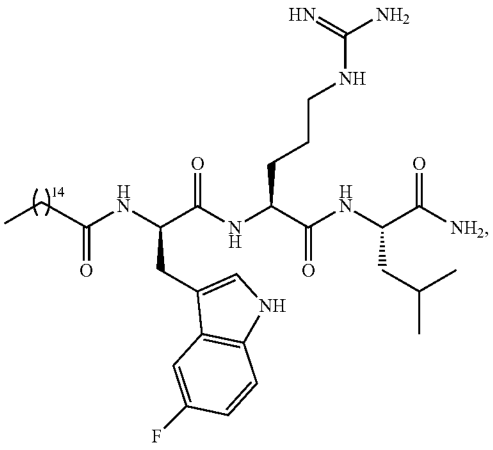
(I-j)
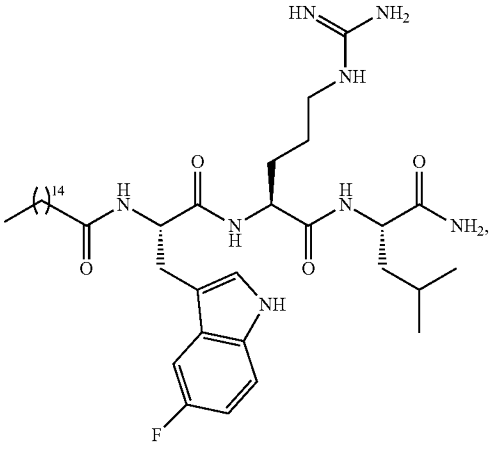
(I-k)
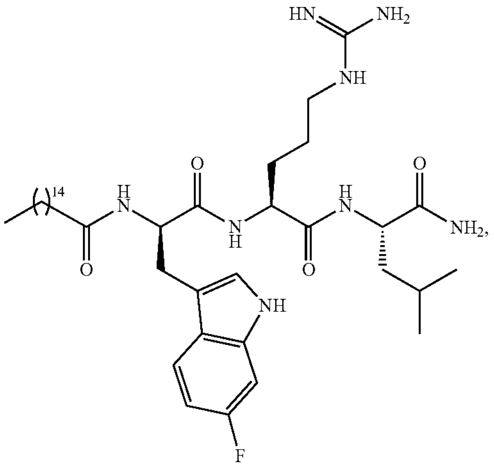

-continued
(I-l)
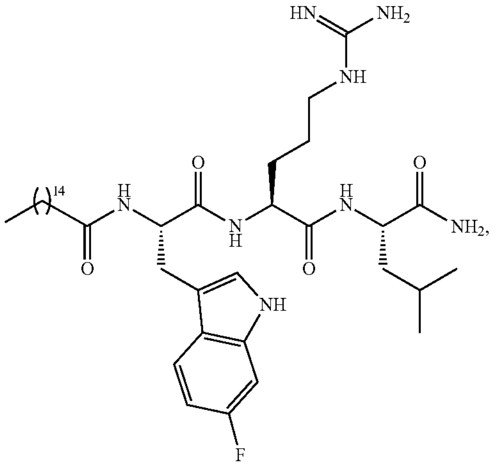
(I-m)
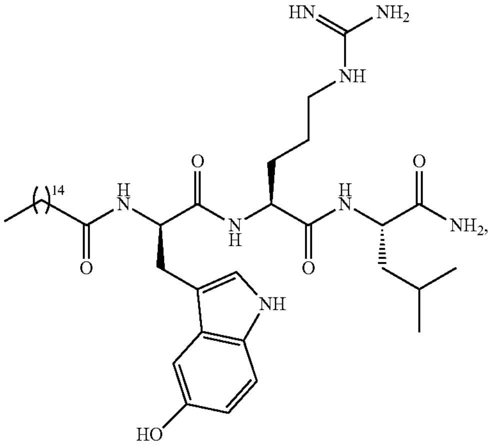
(I-n)
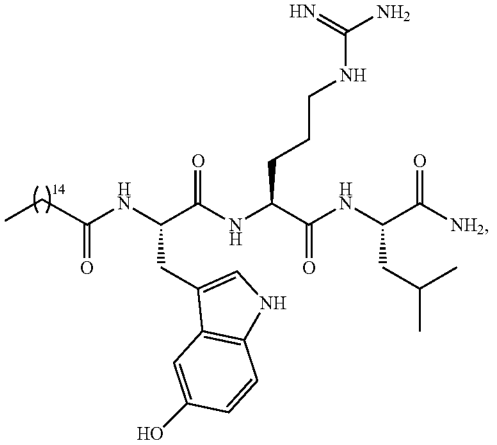
-continued
(I-o)
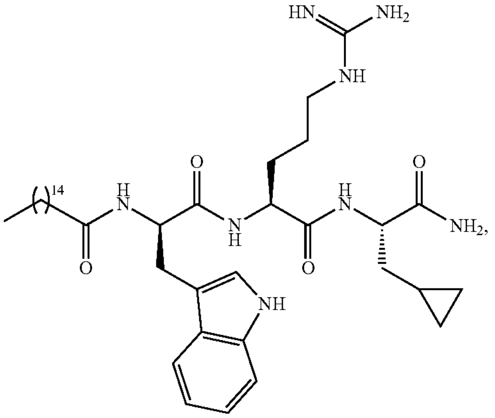
(I-p)
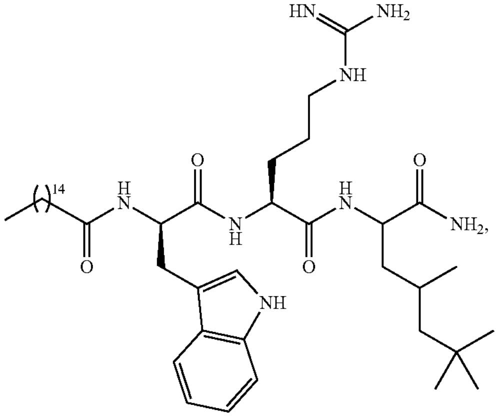
(I-q)
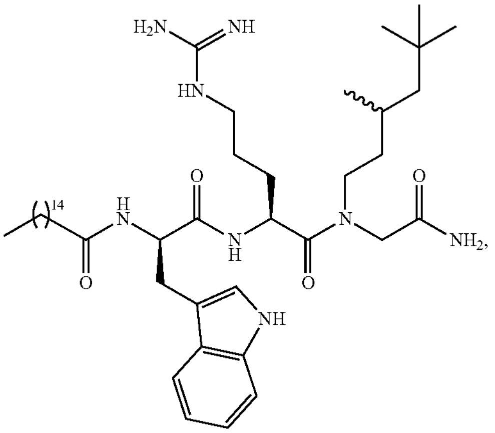

-continued (I-r)

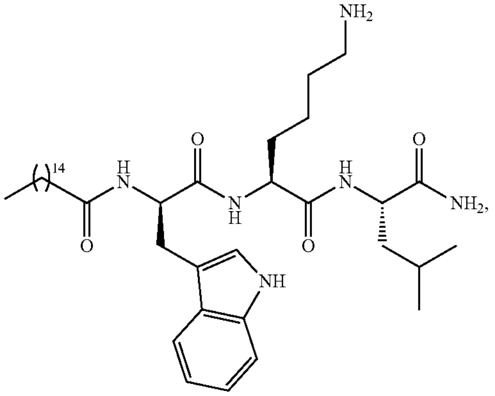

(I-s)

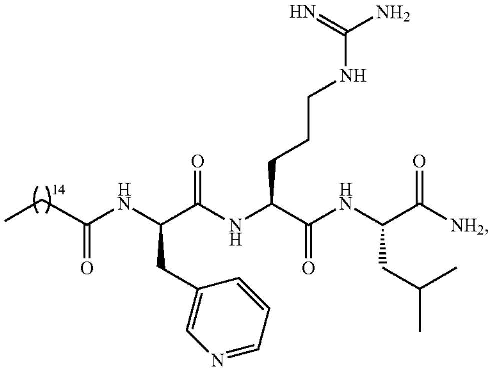

(I-t)

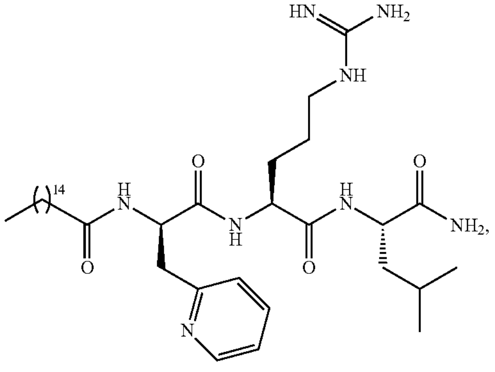

(I-u)

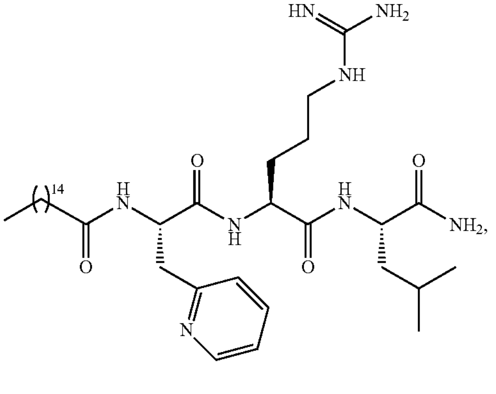

-continued (I-v)

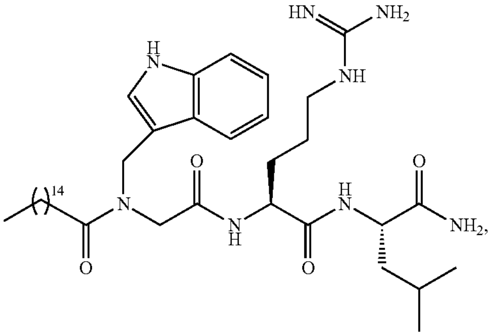

(I-w)

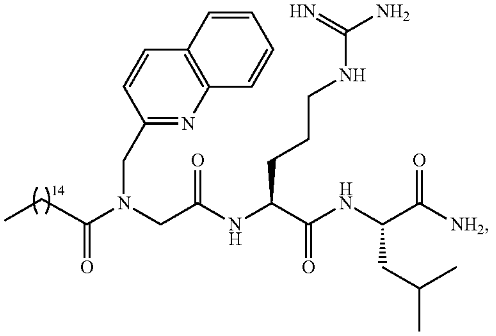

or (I-x)

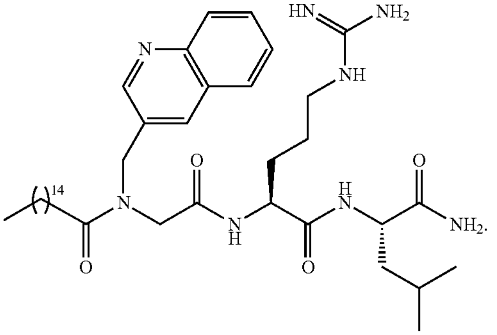

10. The compound according to claim 1, wherein $R^4$ is H or $CH_3$.

11. The compound according to claim 1, wherein the amino acid side chain is selected from the side chains of arginine and lysine.

12. The compound according to claim 1, wherein $R^6$ is H or 3,5,5-trimethylhexyl.

13. The compound according to claim 1, wherein $R^7$ is selected from the group consisting of H, isobutyl, 2,4,4-trimethylpentyl and cyclopropylmethyl.

14. A cosmetic composition comprising at least one compound according to claim 1 and a cosmetically acceptable carrier.

15. The cosmetic composition according to claim 14, wherein the total amount of the at least one compound of formula (I) is in a range of about 0.00001 to 0.5 wt.-%, based on the total weight of the cosmetic composition.

16. The cosmetic composition according to claim 14, wherein the total amount of the at least one compound of formula (I) is in a range of 0.0001 to 0.25 wt.-%, based on the total weight of the cosmetic composition.

17. The cosmetic composition according to claim 14, wherein the total amount of at least one compound of formula (I) is in a range of 0.0001 to 0.1 wt.-%, based on the total weight of the cosmetic composition.

18. The cosmetic composition according to claim 14, wherein the composition further comprises at least one ingredient selected from the group consisting of polysilicones-15, phenylbenzimidazol sulfonic acid, 3-benzylidene camphor, octocrylene, ethylhexyl methoxycinnamate, ethyl hexylsalicylate, homosalate, zinc oxide, bis-ethylhexyloxyphenol methoxyphenyl triazine, methylene bis-benzotriazolyl tetramethylbutylphenol, titanium dioxide, butyl methoxydibenzoylmethane, niacinamide, arbutin, resveratrol, vitamin C (ascorbic acid) as well as derivatives thereof, (skin whitening) plant extracts, retinol, thymus hydrolysate as well as mixtures thereof.

19. A method for the treatment of senile lentigines, for smoothening skin color irregularities and/or for lightening the natural skin color, said method comprising the step of applying a cosmetic composition according to claim 14 to the affected area.

* * * * *